(12) United States Patent
Park et al.

(10) Patent No.: US 8,211,641 B2
(45) Date of Patent: Jul. 3, 2012

(54) METHOD FOR THE DIAGNOSIS OF PREECLAMPSIA

(75) Inventors: Won Sun Park, Busan (KR); Na Ri Kim, Busan (KR); Mohamad Warda, Busan (KR); Jin Han, Busan (KR)

(73) Assignee: Inje University Industry-Academic Cooperation Foundation, Gimhae (KR)

( * ) Notice: Subject to any disclaimer, the term of this patent is extended or adjusted under 35 U.S.C. 154(b) by 0 days.

(21) Appl. No.: 13/037,141

(22) Filed: Feb. 28, 2011

(65) Prior Publication Data

US 2011/0269136 A1 Nov. 3, 2011

Related U.S. Application Data

(62) Division of application No. 12/218,218, filed on Jul. 10, 2008, now abandoned.

(30) Foreign Application Priority Data

Jul. 10, 2007 (KR) .................. 10-2007-0069002

(51) Int. Cl.
 C12Q 1/68 (2006.01)
 C12P 19/34 (2006.01)
 C07H 21/02 (2006.01)
 C07H 21/04 (2006.01)

(52) U.S. Cl. ...... 435/6.11; 435/6.1; 435/6.12; 435/6.18; 435/91.21; 536/23.2; 536/23.5; 536/24.31

(58) Field of Classification Search .................. None
See application file for complete search history.

(56) References Cited

OTHER PUBLICATIONS

Liu et al. Clinical Immunology. 2004. 112: 225-230.*
Coleman et al. Drug Discovery Today. 2003. 8: 233-235.*
Saetre et al. Molecular Brain Research. 2004. 126: 198-206.*
Min et al. BMC Genomics. 2010. 11:96.*
Geisler et al. Cell Tissue Research. 1997. 289: 173-183.*
Haynes et al Electrophoresis. 1998. 19: 1862-1871.*
Gokmen-Polar et al. Cancer Research. 2001. 61: 1375-1381.*
Xu et al., "Mutational Study of Heparan Sulfate 2-O-Sulfotransferase and Chondroitin Sulfate 2-O-Sulfotransferase", Journal of Biological Chemistry, vol. 282, No. 11, Mar. 16, 2007, pp. 8356-8367.
Bao et al., "A Functional Dermatan Sulfate Epitope Containing Iduronate(2-O-sulfate) α1-3GalNAc(6-O-sulfate) Disaccharide in the Mouse Brain", Journal of Biological Chemistry, vol. 280, No. 24, Jun. 17, 2005, pp. 23184-23193.
Kobayashi et al., "Molecular Cloning and Characterization of a Human Uronyl 2-Sulfotransferase That Sulfates Iduronyl and Glucuronyl Residues in Dermatan/Chondroitin Sulfate", Journal of Biological Chemistry, vol. 274, No. 15, Apr. 9, 1999, pp. 10474-10480.
Ohtake et al., "Recognition of Sulfation Pattern of Chondroitin Sulfate by Uronosyl 2-O-Sulfotransferase", Journal of Biological Chemistry, vol. 280, No. 47, Nov. 25, 2005, pp. 39115-39123.

* cited by examiner

*Primary Examiner* — Carla Myers
(74) *Attorney, Agent, or Firm* — Dickinson Wright PLLC

(57) ABSTRACT

The present invention relates to a biomarker and a composition for diagnosis of preeclampsia. In accordance with one aspect of the present invention, there is provided a biomarker for diagnosis of preeclampsia using an enzyme selected from the group consisting of placental chondroitin 4-O-sulfotransferase 1 (C4ST), chondroitin 6-sulfotransferase (C6S), heparan sulfate 6-O-sulfotransferase 1 (HS6S), and dermatan/chondroitin sulfate 2-sulfotransferase (CS-2OST), or uronic acid-2-sulfate (UA2S).

2 Claims, 3 Drawing Sheets

METHOD FOR THE DIAGNOSIS OF PREECLAMPSIA

CROSS-REFERENCE TO RELATED APPLICATION

The present application is a divisional application of application Ser. No. 12/218,218 filed on Jul. 10, 2008 now abandoned, which claims priority under 35 U.S.C. §119(a) to an application filed in the Korean Intellectual Property Office on Jul. 10, 2007 and assigned Korean Patent Application No. 10-2007-0069002, the contents of which are incorporated herein by reference.

SEQUENCE LISTING

The instant application contains a Sequence Listing which has been submitted via EFS-Web and is hereby incorporated by reference in its entirety. Said ASCII copy, created on May 16, 2011, is named sequence 1029008div.txt and is 2,570 bytes in size.

FIELD OF THE INVENTION

The present invention relates to a biomarker and a composition for diagnosis of preeclampsia.

BACKGROUND OF THE INVENTION

Preeclampsia in pregnancy can be a very serious health problem. It can cause fetal growth restriction, fetal death and morbidity, premature deliveries, and death of the mother. The exact cause of preeclampsia is not known, and treatments for efficiently curing or preventing preeclampsia are not also available yet. Preeclampsia is known to cause several problems at the same time, such as high blood pressure (hypertension), pathological edema and leakage of protein into the urine (proteinuria). Further, preeclampsia is one of the pregnancy complications that bring hypertension, proteinuria and traumatism to the mother. It is known that preeclampsia occurs to only about 3-5% of pregnant women, but it can seriously affect both the mother and her unborn (or newborn) baby, and thus, acts as a major cause of increasing perinatal mortality and morbidity rates.

Globally, at least 200,000 pregnant women die from preeclampsia every year. Its symptoms typically become evident after the $20^{th}$ week of pregnancy. Preeclampsia is usually diagnosed by detecting high blood pressure of a pregnant woman or by checking her urine for protein. Early diagnosis and timely treatment of preeclampsia can remarkably reduce risks to the mother and her unborn baby, but such a monitoring method by using those symptoms as criteria is not effective for an early diagnosis of preeclampsia. Further, no treatments are currently available to cure preeclampsia. Preeclampsia can be mild, but potentially life-threatening depending on the severity of the disease. Despite such clinical risks, however, it is difficult to find the cause or the pathogenesis of preeclampsia at an early stage, or to make an early diagnosis and prognosis.

Therefore, if it becomes possible to suggest the pathogenesis of preeclampsia and make an early diagnosis and prognosis based on the same, the mother having preeclampsia and her unborn baby can be protected, and the death rate would be reduced. Even if many researches have been conducted to monitor and predict the occurrence of preeclampsia, they are limited to using a specific protein or substance, which is not sufficient to explain the whole phenomenon about the occurrence of preeclampsia and the pathogenesis thereof.

While the inventors of the present invention are trying to discover the pathogenesis of preeclampsia through the comparison between normal pregnant women and patients with preeclampsia (whether mild or severe), they have learned that the patients with preeclampsia express lower amounts of diverse glycosaminoglycans (GAGs) in the placenta and placenta enzymes responsible for sulfonation of GAGs. Based on this, the inventors developed a new way for the early diagnosis and prognosis of preeclampsia by preparing a biomarker and a composition.

SUMMARY OF THE INVENTION

It is, therefore, a primary object of the present invention to provide a novel biomarker to detect preeclampsia developed in the placenta of a pregnant woman.

It is another object of the present invention to provide a composition for the diagnosis of preeclampsia based on the amounts of diverse GAGs in the placenta and placenta enzymes responsible for sulfonation of GAGs.

It is still another object of the present invention to provide a predictive biomarker kit capable of predicting a risk of preeclampsia.

In accordance with one aspect of the present invention, there is provided a biomarker for diagnosis of preeclampsia using an enzyme selected from the group consisting of placental chondroitin 4-O-sulfotransferase 1 (C4ST), chondroitin 6-sulfotransferase (C6S), heparan sulfate 6-O-sulfotransferase 1 (HS6S), and dermatan/chondroitin sulfate 2-sulfotransferase (CS-2OST), or uronic acid-2-sulfate (UA2S).

In accordance with another aspect of the present invention, there is provided a composition for diagnosis of preeclampsia, comprising one or more primer pairs selected from the group consisting of primer pairs with the sequences of: (Primer Pair No. 1) Forward: 5'GTGGGGAGAGG-GAGAGAATC3'(Sequence No. 1), Reverse: 5'ACAGA-CAAGAACGACCCATC3' (Sequence No. 2); (Primer Pair No. 2) Forward: 5'CCCAAAGTCAGAAAGCGAAG3' (Sequence No. 3), Reverse: 5'ACAAGCAAACCCAC-CAACTC3'(Sequence No. 4); (Primer Pair No. 3) Forward: 5'TCTGAGCCTGACCACAGATG3' (Sequence No. 5), Reverse: 5'CACCTGCACGAACTCAGGA3' (Sequence No. 6); (Primer Pair No. 4) Forward: 5'CCCAGTGGC-CCTAAAGTACA3' (Sequence No. 7), Reverse: 5'GTCCAT-CACTTTGGCAGGTT3' (Sequence No. 8); and (Primer Pair No. 5) Forward: 5'GTACAACCTGGCCAACAACC3' (Sequence No. 9), Reverse: 5'CGCGTGCTATTGTACTGCAT3' (Sequence No. 10).

BRIEF DESCRIPTION OF THE DRAWINGS

The above and other objects and features of the present invention will become apparent from the following description of the preferred examples given in conjunction with the accompanying drawings, in which.

DETAILED DESCRIPTION OF THE PREFERRED EMBODIMENTS

Figure 1:
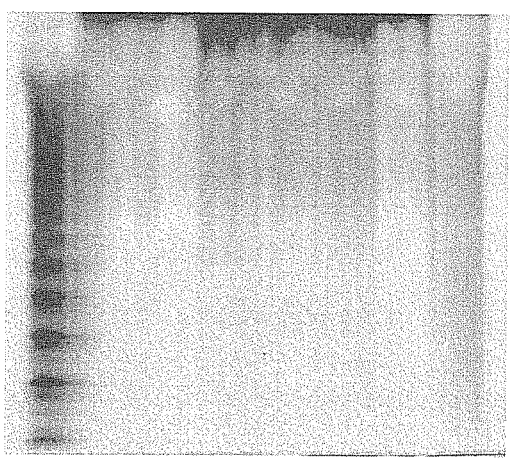
FIG. 1 shows a polyacrylamide gel electrophoresis (PAGE) assay picture of a GAG isolated from other tissue (where lane std denotes a heparin oligosaccharide standard, lanes 1 to 12 correspond to GAGs from sample #1 to #12 (refer to Table 2), and lane HS denotes a heparan sulfate control group)
Figure 1:
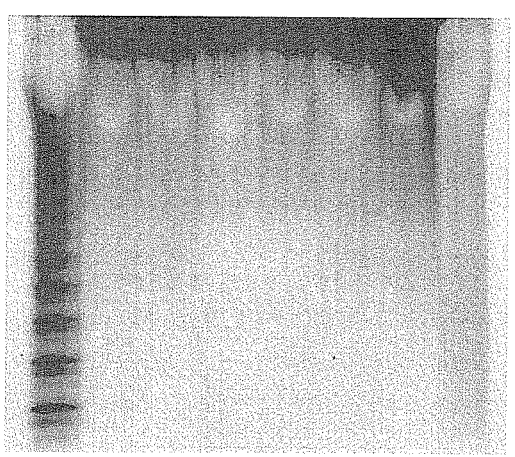

In the following detailed description, reference is made to the accompanying drawings and sequence listing that show, by way of illustration, specific embodiments in which the invention may be practiced. These embodiments are described in sufficient detail to enable those skilled in the art to practice the invention. It is to be understood that the various embodiments of the invention, although different, are not necessarily mutually exclusive. The following detailed description is, therefore, not to be taken in a limiting sense, and the scope of the present invention is defined only by the appended claims that should be appropriately interpreted along with the full range of equivalents to which the claims are entitled.

Then, experiments performed for better understanding the present invention will be described in detail as follows, which are set forth to illustrate, but are not to be construed to limit the present invention.

The inventors confirmed by using RT-PCR that patients who developed preeclampsia expressed a lower amount of placenta enzymes, which are involved in sulfonation of GAGs. GAGs cover plasma membranes of all cells and fill extracellular matrix composed of heparin sulfate (HS), CS, and dermatan sulfate (DS). The inventors confirmed that mRNA levels of C4ST, C6S, HS6S and CS-2OST were reduced in patients with preeclampsia. Particularly, the inventors turned out that patients with preeclampsia did not have other isoforms of the last enzyme (i.e., CS-2OST), which cause C2-sulfonation on uronic acid or iduronic acid in CS with disaccharide repeat units. This decrease in the amount of the enzyme was confirmed through the lack of UA2S in a placental sample tested for preeclampsia.

Further, the inventors learned from RT-PCR assay results that the amount of CS-2OST was noticeably decreased in the placenta of a woman affected by preeclampsia (this was also the same for other GAG sulfotransferases). The inventors also confirmed through the disaccharide assay that UA2S (the final product of sulfate 2-sulfotransferase), which is the disaccharide repeat unit of placental GAGs, was completely disappeared from a disease-infected sample.

The inventors assumed that preeclampsia might be associated with the progress of glycomics of the placental abnormalities. This assumption was confirmed by monitoring decrease in the placental mRNA expression of diverse GAG sulfotransferases in preeclamptic pregnancy.

One of the important findings through the analysis of CS disaccharide composition for this invention is that preeclamptic pregnancies lack the expression of UA2S, and this supports parallel decrease observed in the expression of CS-2OST. This is very clear in that the enzyme has only a single heteroplasm in most entities with known genome sequences, which is contradictory to its various heteroplasms in almost all other chondroitin sulfotransferases (see Xu, D. et al., J. Biol. Chem., Mar. 16, 2007; 282(11): 8356-67). Along with complicated functions that are verified in diverse manners (see Bao, X. et al., (2005), J. Biol. Chem., 280, 23184-23193), CS-2OST carries a sulfo group to the 2-OH position of hexauronic acid adjacent to a N-acetylated galactosamine residue carrying 6-O or 4-O sulfo group (see Kobayashi, M. et al., (1999), J. Biol. Chem., 274, 10474-10480; Ohtake, S. et al., (2005), J. Biol. Chem., 280, 39115-39123).

Interestingly enough, the clear superimposing image of a decreased CS-2OST mRNA expression, as the last step of CS variation in addition to the absence of UA2S subcluster in CS under preeclampsia, reflects a poor, final tuning of CS that occurs commonly in the placenta of a pregnant woman. No one has yet discovered like the inventors that there is decrease in the expression of sulfotransferases under preeclampsia. What is new and interesting is that the decrease in the mRNA expression of CS-2OST enzyme in the placenta of the pregnant woman with preeclampsia is in parallel with complete absence of its byproduct, UA2S. The use of such data makes it possible to develop a predictive biomarker kit through which the risk of preeclampsia in a pregnant woman can be predicted.

To this end, the inventors obtained placental samples from normal pregnant women and from patients who are epidemiologically diagnosed with preeclampsia. Those samples were ground, fats were removed therefrom, proteins were hydrolyzed, and various GAGs were isolated by using a column chromatography. These isolated GAGs were quantified by carbazole assay (Blyscan assay) (refer to Table 1). In result, the average amount of GAGs (mg/g; dry sample) was lower in preeclampsia samples than that of the control group.

In addition, for the analysis of a molecular weight and polydispersity of a sample, the inventors conducted PAGE, and computed an average molecular weight of GAGs based on the heparin oligosaccharide standard (refer to FIG. 1). In result, the average molecular weight of GAGs was slightly lower in preeclampsia samples than that of the control group (refer to Table 2).

Figure 2:
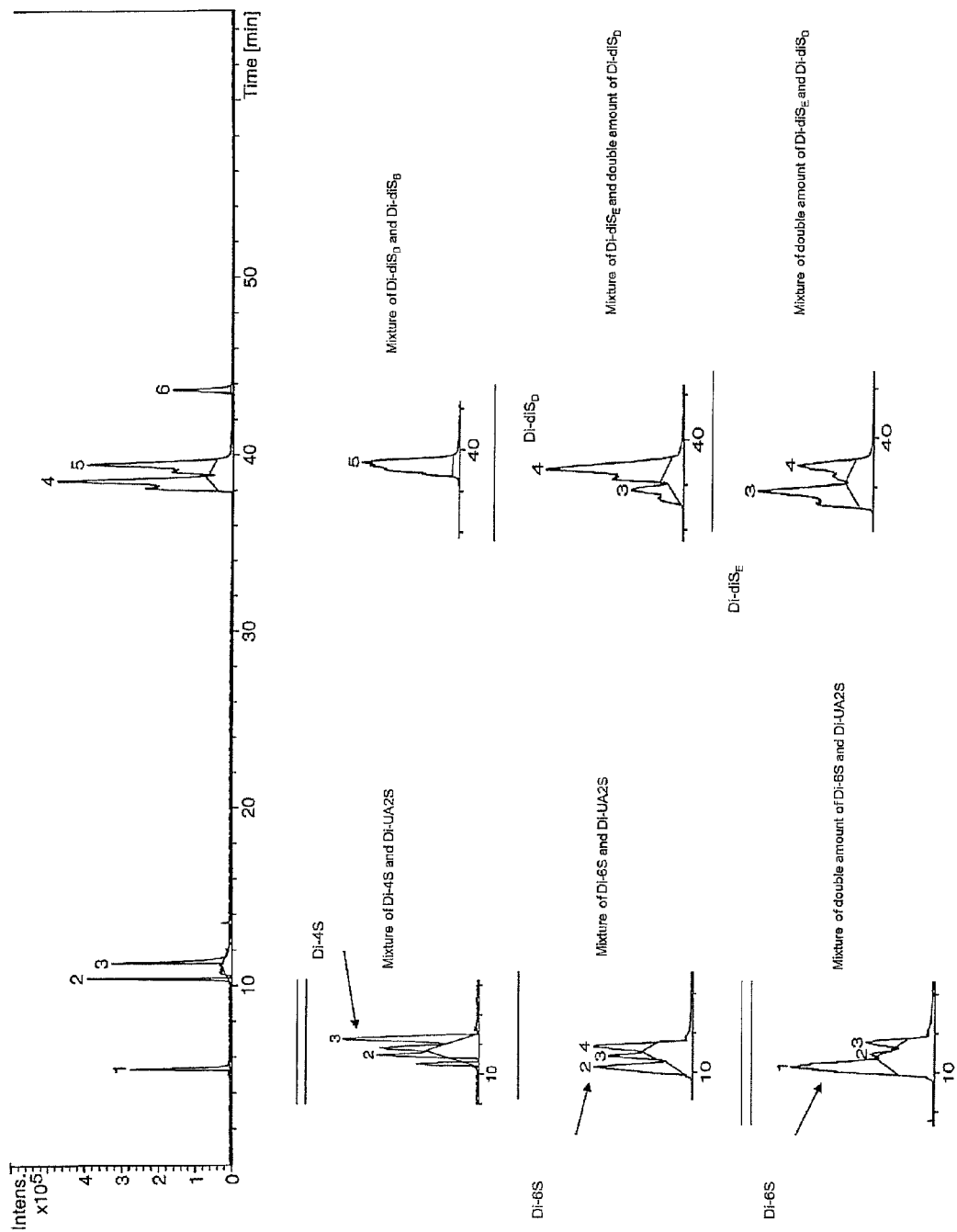
FIG. 2 represents a chromatographic result of CS (chondroitin sulfates) disaccharide standard.

Then, the inventors depolymerized the GAG complex enzymatically, and conducted a disaccharide analysis using LC-MS (refer to FIG. 2). In doing so, 8 kinds of disaccharides of Hep/HS were isolated (refer to FIG. 3).

A total of 12 samples were subjected to a compositional analysis of CS disaccharides (refer to FIG. 2), wherein the compositional analysis was measured in terms of Mean/SD (refer to Table 3). The comparison of CS disaccharides between the preeclampsia sample group and the control group shows that samples in the control group have more UA2S and TriS than samples in the preeclampsia group (refer to Table 4). On the other hand, Hp/HS disaccharides have N-sulfo disaccharides that are more abundant in the control group than in the preeclampsia sample group. This implies that translocation of the N-sulfo group under preeclampsia occurs most frequently at the sixth carbon position. The preeclampsia samples are very rich in tri-sulfo disaccharides (refer to Table 5).

The inventors also examined the variation in the amount of mRNA of diverse GAG synthesis regulatory enzymes by Quantitative Real-Time PCR (qRT-PCR). All primers were designed using gene-specific sequences fostered by GenBank (refer to Table 6). The RT-PCR result confirms that the preeclampsia samples, compared with the control group placenta, showed noticeable decrease in the expression of diverse chondroitin sulfotransferases enzymes (refer to Table 7).

Hereinafter, the present invention will be explained in more detail through examples. However, it will be apparent to those skilled in the art that these examples are only for the purpose of explaining the present invention in detail, but not intended to limit the scope of the invention.

EXAMPLE 1

Acquisition—Purchase of Samples

Placental samples used for the present invention (e.g., placental samples from normal pregnant women and from patients who are epidemiologically diagnosed with preeclampsia) were provided by the department of obstetrics and gynecology in Inje University Hospital.

Actinase E was purchased from Kaken Biochemicals (Tokyo, Japan), CS, chondroitin lyases and heparin lyases were purchased from Seikagaku (Tokyo, Japan), and polyacrylamide, urea, CHAPS, Alcian blue dye, 2-cyanoacetamide and tetra-n-butylamonium hydrogen sulfate were purchased from Sigma Chemical Company (St. Louis, Mo.). All other samples were of reagent grade. Vivapure MAXI QH columns were purchased from Viva science (Edgewood, N.J.).

Unsaturated disaccharide standards from CS (Di-0S ΔUA-Gal, Di-4S ΔUA-Gal4S, Di-6S ΔUA-Gal6S, Di-UA2S ΔUA2S-Gal, Di-diS$_B$ ΔUA2-Gal4S, Di-diS$_D$ ΔUA 2S-Gal6S, Di-diS$_E$ ΔUA-Gal4S6S, Di-triS ΔUA2S-Gal4S6S) were purchased from Seikagaku Corporation (Japan), and chondroitinase ABC and ACII were also purchased from Seikagaku Corporation (Japan).

Unsaturated disaccharide standards from Hep/HS (Di-0S ΔUA-GlcNAc, Di-NS ΔUA-GlcNS, Di-6S ΔUA-GlcNAc6S, Di-UA2S ΔUA2S-GlcNAc, Di-UA2SNS ΔUA2S-GlcNS, Di-NS6S ΔUA-GlcNS6S, Di-UA2S6S ΔUA2S-GlcNAc6S, Di-triS ΔUA2S-GlcNS6S) were purchased from Seikagaku Corporation (Japan).

A mixture (150 ng/μl) of disaccharide standards containing Di-0S, Di-4S, Di-6S, Di-diS$_D$, Di-diS$_E$ and Di-triS was indicated as std1. A mixture of disaccharide standards containing Di-0S, Di-4S, Di-UA2S, Di-diS$_D$, Di-diS$_E$, and Di-triS was indicated as std2. A mixture of disaccharide standards containing Di-0S, Di-4S, Di-6S, Di-diS$_B$, Di-diS$_D$, and Di-triS was indicated as std3. A mixture of disaccharide standards containing Di-0S, Di-4S, Di-UA2S, Di-diS$_B$, Di-diS$_E$, and Di-triS was indicated as std4. A mixture of disaccharide standards containing Di-4S, Di-diS$_E$, and double the amount of Di-6S and Di-diS$_D$ was indicated as std5. A mixture of disaccharide standards containing Di-6S, Di-diS$_D$, and double the amount of Di-4S and Di-diS$_E$ was indicated as std6. A mixture of disaccharide standards containing Di-UA2S and double the amount of Di-6S was indicated as std7.

EXAMPLE 2

Isolation and Purification of GAG

With the use of mortars and pestles, the samples were pulverized together with dry ice to very fine particles of uniform size. Tissues were rinsed with a mix solution of chloroformlmethanol (2:1, 1:1, and 1:2) (v/v), respectively, overnight, and thus defatted.

In 5 ml water, the fat-free samples were treated with 1% Actinase E (20 mg/ml) at 55° C. for 18 hours to hydrolyze protein. Following the hydrolysis of protein, dry urea and dry'CHAPS (2 wt % CHAPS and 8 M urea) were added to each of the samples. The obtained blurring solutions passed through a syringe filter having a 0.2 μm film, and thus became transparent. Vivapure MAXI QH spin columns reached the equilibrium state with the addition of 3 ml of 8 M urea (pH 8.3) containing 2% CHAPS. The clear, filtered samples were loaded on the Vivapure MAXI QH spin columns in a centrifugal separator (500×g) and then perfused. First, the columns were rinsed with 3 ml of 8 M urea (pH 8.3) containing 2% CHAPS at pH 8.3. Then, they were rinsed five times with 5 ml of 200 mM NaCl. Further, the samples were rinsed three times with 1 ml of 16% NaCl to emit GAG from the spin column. To prepare an 80 vol % solution, 12 ml of methanol was added to each sample, and the mix solutions were allowed to reach the equilibrium state over the period of 18 hours at 4° C. The obtained precipitates were centrifuged at 2500×g for 15 min and collected. The precipitates were dissolved in 0.5 ml water and collected. The collected precipitates were put in a freezer for additional analysis on the collected GAGs.

EXAMPLE 3

Quantification of GAGS by Carbazole Assay (Blyscan Assay)

With the isolated GAGs as a marker dye, the inventors conducted Blyscan assay using 1,9-dimethylmethylene blue (DMB) and quantified the amount of GAG in each of the samples by using standard CS.

As shown in Table 1 below, the inventors turned out that the average amount of GAGs (mg/g; dry samples) in the control group was 2.78±0.48 mg/g, and the average amount of GAGs in the preeclampsia samples was 2.26±0.21 mg/g.

TABLE 1

| No. | Description on sample | Original mass (g) | Dry mass (g) | GAG (mg) | GAG (mg)/g | MW (KD) |
|---|---|---|---|---|---|---|
| 1 | Normal control group A, Sample 1 | 0.9729 | 0.1094 | 0.205 | 1.87 | 8.4 |
| 2 | Normal control group A, Sample 2 | 1.0842 | 0.1136 | 0.305 | 2.68 | 8.7 |
| 3 | Normal control group B, Sample 1 | 0.78 | 0.0817 | 0.226 | 2.77 | 1.3 |
| 4 | Normal control group B, Sample 2 | 0.73 | 0.081 | 0.283 | 3.49 | 10.0 |
| 5 | Normal control group C, Sample 1 | 0.769 | 0.0694 | 0.197 | 2.84 | 10.0 |
| 6 | Normal control group C, Sample 2 | 0.545 | 0.063 | 0.190 | 3.0 | 10.0 |
| 7 | Preeclampsia patient A, Sample 1 | 1.26 | 0.109 | 0.211 | 1.94 | 9.3 |
| 8 | Preeclampsia patient A, Sample 2 | 1.1 | 0.099 | 0.233 | 2.35 | 9.7 |
| 9 | Preeclampsia patient B, Sample 1 | 0.795 | 0.094 | 0.200 | 2.13 | 9.6 |
| 10 | Preeclampsia patient B, Sample 2 | 0.93 | 0.109 | 0.229 | 2.1 | 9.7 |
| 11 | Preeclampsia patient C, Sample 1 | 1.18 | 0.116 | 0.287 | 2.47 | 9.3 |
| 12 | Preeclampsia patient C, Sample 2 | 1.05 | 0.116 | 0.295 | 2.54 | 9.3 |

EXAMPLE 4

PAGE Assay

For the analysis of a molecular weight and polydispersity of each sample, PAGE assay was conducted. Electrophoresis of about 5 mg of GAG isolated to each lane was performed on the enzymatically prepared heparin oligosaccharide standard from bovine lung heparin. Then, gel visualized by Alcian blue was digitized with UN-Scan-it software (Silk Scientific, Utah, US), and the average molecular weight of GAGs was computed based on the heparin oligosaccharide standard (refer to FIG. 1).

In result, as described in Table 2, an average molecular weight of GAGs from the control group and an average molecular weight of GAGs from the preeclampsia samples were 9.57±0.73 kD and 9.48±0.19 kD, respectively.

EXAMPLE 5

Disaccharide Assay Using LC-MS

<5-1> Enzymatic De-polymerization of Complex GAG

The purified GAGs (20 μg/μl) were decomposed additionally by chondroitinase ABC 10U and ACII (SIGMA) and dissolved in 500 μl of 0.1% BSA, respectively. 5 μl of chondroitinase ABC and 5 μl of ACII were added, as enzyme solutions, to 20 μl of a substrate and allowed for the reaction overnight at 37° C. The products were then filtered by a centrifugal filter device (3000 Da cutoff, Millipore Corporation) to thus yield CS disaccharides. An accurately measured 100 μl of dd H$_2$O was added, and thereafter, the disaccharides were freeze-dried. Then, heparinase I, II, and III (Sigma) were added to the residual and allowed for the reaction overnight at 37° C. Also, the products were filtered by the centrifugal filter device (3000 Da cutoff, Millipore Corporation) to thereby yield Hep/HS disaccharides.

<5-2> LC-MS Assay

The LC-MS assay was conducted through LC-MS system (Agilent LC/MSD trap MS). Solutions A and B for HPLC were 15% and 70%, respectively, each containing 37.5 mM NH$_4$CO$_3$ and 11.25 mM Tributylamine at the same concentration. The pH values of the solutions were adjusted to 6.5 with acetic acid. A flow rate was 10 μl/min. Separation was conducted using a C-18 column (Agilent) for 20 min for the solution A, followed by 20-45 min for the solution B with the slope of a straight line from 0% to 50%. Column effluent returned to the source of EMI-MS to continue monitoring.

In result, in standard chromatography (refer to the top panel in FIG. 2), Di-0S appeared at 5.3-5.4 min. Disaccharides having a single sulfate, such as Di-UA2S, Di-4S and Di-6S, appeared at 10.3-12.5 min. Disulfated disaccharides like Di-diS$_D$, Di-diS$_D$ and Di-diS$_E$ appeared at 10.3-12.5 min. Trisulfated disaccharide Di-triS appeared lastly at about 43.7 min. According to standard chromatograph of another mix solution, Di-4S appeared at 11 min, Di-6S appeared at 10.3 min, and the peak at the center was Di-UA2S. Di-diS$_E$ appeared at about 38.6 min, and Di-diS$_E$ and Di-diS$_D$ appeared together at 39.5 min.

Figure 3:
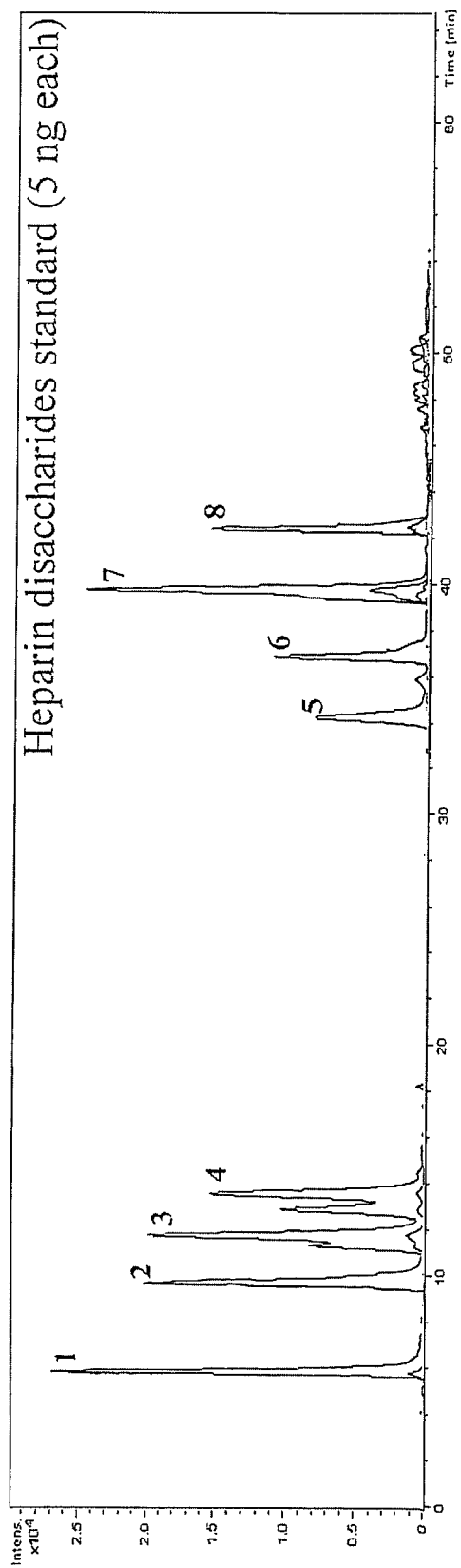
FIG. 3 presents a chromatographic result of Hep/HS disaccharide standard.

FIG. 3 shows 8 kinds of disaccharides well isolated from Hep/HS. All fractions were confirmed by MS (where data is not shown).

It is evident from the comparison on CS disaccharides between the sample group and the control group that the control group samples are more abundant in UA2S and TriS than the preeclampsia samples (refer to Table 4). In addition, it was verified that Hp/HS disaccharides have N-sulfo disaccharides that are more abundant in the control group compared with the preeclampsia sample group. This result supports that translocation of the N-sulfo group under preeclampsia occurs most frequently at the sixth carbon position. Interestingly enough, as shown in Table 5, one of the preeclampsia samples had a very large amount of tri-sulfo disaccharide.

Tables 2 to 5 below show compositional analysis of CS disaccharides on all 12 samples, compositional analysis of CS disaccharides in terms of Mean/SD, compositional analysis of Hp/HS disaccharides on all 12 samples, and compositional analysis of Hp/HS disaccharides in terms of Mean/SD, respectively.

TABLE 2

|  | 0S | 6S | UA2S | 4S | diS$_E$ | diS$_D$ or diS$_D$ | triS | TPA |
|---|---|---|---|---|---|---|---|---|
| Control group | | | | | | | | |
| 1 | n.d | 42.6% | n.d | 57.4% | n.d | n.d | n.d | 1715 |
| 2 | n.d | 16% | 39.3% | 42.7% | n.d | n.d | 2% | 24637 |
| Mean | n.d | 29.3% | 19.7% | 50.1% | n.d | n.d | 1% | 13176 |
| 3 | 1.3% | 4.1% | 8.8% | 83.7% | n.d | n.d | 2.1% | 16627 |
| 4 | n.d | 37.2% | n.d | 62.1% | n.d | n.d | 0.7% | 32478 |
| Mean | 0.7% | 20.7% | 4.4% | 72.9% | n.d | n.d | 1.4% | 24552 |
| 5 | 2.9% | 24.4% | n.d | 66.5% | n.d | n.d | 6.1% | 5926 |
| 6 | n.d | 46.2% | n.d | 46.8% | n.d | n.d | 7% | 5443 |
| Mean | 1.5% | 35.3% | n.d | 56.7% | n.d | n.d | 6.5% | 5684 |
| Preeclampsia | | | | | | | | |
| 7 | n.d | 44.7% | n.d | 54.7% | n.d | n.d | 0.6% | 68532 |
| 8 | n.d | 49.2% | n.d | 50.8% | n.d | n.d | 0.2% | 169810 |
| Mean | n.d | 47% | n.d | 52.7% | n.d | n.d | 0.4% | 119171 |
| 9 | n.d | 32.2% | n.d | 66.5% | n.d | n.d | 1.2% | 30556 |
| 10 | 0.3% | 37% | n.d | 62.4% | n.d | n.d | 0.2% | 101902 |
| Mean | 0.15% | 34.6% | n.d | 64.5% | n.d | n.d | 0.7% | 66229 |
| 11 | n.d | 43.3% | n.d | 56.7% | n.d | n.d | n.d | 236590 |
| 12 | n.d | 42.4% | n.d | 57.6% | n.d | n.d | n.d | 187563 |
| Mean | n.d | 42.9% | n.d | 57.1% | n.d | n.d | n.d | 212076 |

TABLE 3

|  |  | 0S | 6S | UA2S | 4S | diS$_E$ | diS$_D$ or diSD | triS | TPA |
|---|---|---|---|---|---|---|---|---|---|
| Control group | Mean | 0.7% | 28.4% | 8% | 59.9% | n.d | n.d | 2.98% | 14471 |
|  | ±SD | 0.7% | 0.7% | 10.3% | 11.8% | 0 | 0 | 3.1% |  |
| Preeclampsia | Mean | n.d | 41.5% | n.d | 58.1% | n.d | n.d | 0.3% | 132492 |
|  | ±SD | 0.1% | 6.3% | 0 | 5.9% | 0 | 0 | 0.3% |  |

TABLE 4

|  | | 0S | NS | 6S | UA2S | UA2SNS | NS6S | UA2S6S | triS | TPA |
|---|---|---|---|---|---|---|---|---|---|---|
| Control group | | | | | | | | | | |
| | 1 | n.d | 63.6% | 36.4% | n.d | n.d | n.d | n.d | n.d | 11579 |
| | 2 | n.d | 74.3% | 25.7% | n.d | n.d | n.d | n.d | n.d | 5114 |
| | Mean | n.d | 69.0% | 31.0% | n.d | n.d | n.d | n.d | n.d | 8346 |
| | 3 | n.d | 48.2% | 51.8% | n.d | n.d | n.d | n.d | n.d | 25163 |
| | 4 | n.d | 34.7% | 60.7% | n.d | 0.4% | n.d | n.d | 4.3% | 54561 |
| | Mean | n.d | 41.5% | 56.2% | n.d | 0.2% | n.d | n.d | 2.1% | 39862 |
| | 5 | n.d | 69.0% | 26.0% | 5.0% | n.d | n.d | n.d | n.d | 17876 |
| | 6 | n.d | 75.5% | 24.5% | n.d | n.d | n.d | n.d | n.d | 9447 |
| | Mean | n.d | 72.3% | 25.2% | 2.5% | n.d | n.d | n.d | n.d | 13661 |
| Preeclampsia | | | | | | | | | | |
| | 7 | n.d | 49.0% | 51.0% | n.d | n.d | n.d | n.d | n.d | 45024 |
| | 8 | n.d | 28.8% | 50.9% | 20.3% | n.d | n.d | n.d | n.d | 104083 |
| | Mean | n.d | 38.9% | 51.0% | 10.1% | n.d | n.d | n.d | n.d | 74553 |
| | 9 | n.d | 12.4% | 84.6% | n.d | 3.0% | n.d | n.d | n.d | 3586 |
| | 10 | n.d | 16.9% | 78.2% | n.d | 1.9% | n.d | n.d | 3.0% | 11064 |
| | Mean | n.d | 14.7% | 81.4% | n.d | 2.5% | n.d | n.d | 0.1% | 7325 |
| | 11 | n.d | 10.8% | 69.9% | n.d | 1.2% | n.d | n.d | 18.1% | 43001 |
| | 12 | n.d | 12.6% | 16.7% | 9.1% | 8.4% | n.d | n.d | 53.1% | 3740 |
| | Mean | n.d | 11.7% | 43.3% | 4.6% | 4.8% | n.d | n.d | 35.6% | 23374 |

TABLE 5

|  |  | 0S | NS | 6S | UA2S | UA2SNS | NS6S | UA2S6S | triS | TPA |
|---|---|---|---|---|---|---|---|---|---|---|
| Control group | Mean | n.d | 60.8% | 37.5% | 0.8% | n.d | n.d | n.d | n.d | 20623 |
| | ±SD | 0 | 16.9% | 16.5% | 1.4% | 0.1% | 0 | 0 | 0 | |
| Preeclampsia | Mean | n.d | 21.8% | 58.6% | 4.9% | 2.4% | n.d | n.d | 12.4% | 35083 |
| | ±SD | 0 | 10.5% | 14.2% | 3.6% | 1.7% | 0 | 0 | 14.2% | |

EXAMPLE 6 qRT-PCR

Variation in the amount of mRNA of diverse GAG synthesis regulatory enzymes was examined by qRT-PCR. Total RNA amount was extracted, using an RNA Ambion RiboPure total RNA isolation kit, from preeclampsia-infected placentas and normal placentas. Following the treatment with deoxyribonuclease I (Takara Holdings Inc., Japan), total RNA was reversely transcribed by SuperScript II reverse transcriptase (Invitrogen, Carlsbad, Calif.). Next, qRT-PCR was conducted using iCycler iQ system (Bio-Rad, Hercules, Calif.). Primers were designed using software Primer 3 (developed by Steve Rozen and Helen J. Skaletsky). All primers were designed using gene-specific sequences fostered by GenBank. The gene expression data was normalized to GAPDH as much as house keeping gene used as an internal standard for research. Primer sequences are presented in Table 6 (forward primers and reverse primers used for qRT-PCR) as follows.

TABLE 6

| | GenBank Accession # | Primer Sequence | | Predicted size (bp) |
|---|---|---|---|---|
| | | Forward direction | Reverse direction | |
| (GAPDH) | NM_002046.3 | 5'ACCACAGTCCAT GCCATCAC3' Sequence No. 1 | 5'TCCACCACCCT GTTGCTGTA3' Sequence No. 2 | 452 |
| Chondroitin 4-O-sulfo-transferase (C4ST) | NM_018413 | 5'GTGGGGAGAGGG AGAGAATC3' Sequence No. 3 | 5'ACAGACAAGAA CGACCCATC3' Sequence No. 4 | 200 |
| Chondroitin 6-sulfo-transferase (C6S) | NM_004273 | 5'CCCAAAGTCAGA AAGCGAAG3' Sequence No. 5 | 5'ACAAGCAAACC CACCAACTC3' Sequence No. 6 | 189 |
| Dermatan/ chondroitin sulfate 2-sulfo-transferase (CS-2OST) | NM_005715 | 5'TCTGAGCCTGAC CACAGATG3' Sequence No. 7 | 5'CACCTGCACAG AACTCAGGA3' Sequence No. 8 | 153 |

TABLE 6 -continued

| GenBank Accession # | Primer Sequence | | Predicted size (bp) |
|---|---|---|---|
| | Forward direction | Reverse direction | |
| Heparan N-deacetyl-ase/N-sulfotrans-ferase-1 (NDST-1) NM_001543 | 5'CCCAGTGGCCCT AAAGTACA3' Sequence No. 9 | 5'GTCCATCACTT TGGCAGGTT3' Sequence No. 10 | 205 |
| Heparan sulfate 6-O-sulfo-transferase 1 (HS6S) NM_004807 | 5'GTACAACCTGGC CAACAACC3' Sequence No. 11 | 5'CGCGTGCTATT GTACTGCAT3' Sequence No. 12 | 243 |

It was verified from the RT-PCR result that the preeclampsia samples, compared with the control group placenta, showed noticeable decrease in the expression of diverse chondroitin sulfotransferases enzymes (refer to Table 7). Although the expression of heparan sulfate 6-O-sulfotransferase in preeclampsia was markedly decreased, NDST-1 mRNA expression showed no significant change even in preeclampsia.

TABLE 7

Quantitative analysis of relative change in mRNA expression of diverse GAG synthesis enzymes based on qRT-PCR of placenta of women with preeclampsia

| | Gene | $C_T^a$ | $\Delta C_T^b$ | $\Delta\Delta C_T^c$ | Relative expression$^d$ to control group |
|---|---|---|---|---|---|
| chondroitin 4-O-sulfotransferase 1 (C4ST) | | | | | |
| Pre-eclampsia | GAPDH | 16.54 ± 0.38 | 5.25 ± 0.61 | 1.35 | 0.39 |
| | C4ST | 21.79 ± 0.24 | | | |
| Control group | GAPDH | 17.43 ± 0.17 | 3.9 ± 0.25 | | |
| | C4ST | 21.33 ± 0.18 | | | |
| chondroitin 6-sulfotransferase (C6S) | | | | | |
| Pre-eclampsia | GAPDH | 16.54 ± 0.38 | 7.913 ± 0.45 | 2.9 | 0.134 |
| | C6S | 24.45 ± 0.61 | | | |
| Control group | GAPDH | 17.43 ± 0.17 | 5 ± 0.6 | | |
| | C6S | 22.43 ± 0.43 | | | |
| dermatan/chondroitin sulfate 2-sulfotransferase (CS-2OST) | | | | | |
| Pre-eclampsia | GAPDH | 16.54 ± 0.38 | 8.45 ± 0.64 | 2.3 | 0.2 |
| | CS2S | 24.99 ± 0.49 | | | |
| Control group | GAPDH | 17.43 ± 0.17 | 6.15 ± 0.70 | | |
| | CS2S | 23.58 ± 0.53 | | | |
| heparan N-deacetylase/N-sulfotransferase-1 (NDST-1) | | | | | |
| Pre-eclampsia | GAPDH | 16.54 ± 0.38 | 3.85 ± 0.29 | 0.167 | 1.123 |
| | HDS-1 | 20.53 ± 0.48 | | | |
| Control group | GAPDH | 17.43 ± 0.17 | 4.02 ± 1.03 | | |
| | HDS-1 | 21.45 ± 0.86 | | | |
| heparan sulfate 6-O-sulfotransferase 1 (HS6ST) | | | | | |
| Pre-eclampsia | GAPDH | 16.54 ± 0.38 | 7.21 ± 1.29 | 1.78 | 0.29 |
| | HS6S | 23.75 ± 1.12 | | | |
| Control group | GAPDH | 17.43 ± 0.17 | 5.43 ±± .02 | | |
| | HS6S | 22.87 ± 0.85 | | | | where a: $C_T$ data average for each sample, b: $\Delta C_T$ value is calculated by subtracting GAPDH $C_1$ from each sample $C_T$, c: $\Delta\Delta C_T$ value is calculated by subtracting control group $\Delta C_T$ from each preeclampsia sample $\Delta C_T$, and d: relative expression to the control group is calculated using equation $2^{-\Delta\Delta C_T}$.

As discussed earlier, the biomarker and composition for diagnosis of preeclampsia according to the present invention are not only effective in the diagnosis of preeclampsia, but also useful for developing a predictive biomarker kit through which the risk of preeclampsia in a pregnant woman can be predicted.

While the invention has been shown and described with respect to the preferred embodiments, it will be understood by those skilled in the art that various changes and modifications may be made without departing from the spirit and the scope of the invention as defined in the following claims.

What is claimed is:

1. A method for identifying preeclampsia of pregnancy in a pregnant woman, the method comprising:
   isolating a placental tissue from the pregnant woman;
   performing RT-PCR assays to detect the level of C4ST in the isolated placental tissue of the pregnant woman;
   measuring an amount of mRNA of the C4ST by Quantitative Real-Time PCR (qRT-PCR); and
   identifying preeclampsia of pregnancy in the pregnant woman based on the amount of mRNA of the C4ST from the isolated placental tissue of the pregnant woman, wherein an amount of mRNA of the C4ST in a placental tissue of a pregnant woman having preeclampsia is lower than an amount of mRNA of the C4ST in a placental tissue of a pregnant woman who does not have preeclampsia.

2. The method of claim 1, further comprising:
   comparing the amount of mRNA of the C4ST in the isolated placental tissue of the pregnant woman with the amount of mRNA of the C4ST in the placental tissue of the pregnant woman who does not have preeclampsia.

* * * * *

```
                         SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: GAPDH forward

<400> SEQUENCE: 1
accacagtcc atgccatcac                                              20

<210> SEQ ID NO 2
<211> LENGTH: 20
<212> TYPE: DNA
<213> ORGANISM: Artificial Sequence
<220> FEATURE:
<223> OTHER INFORMATION: GAPDH backward

<400> SEQUENCE: 2
tccaccaccc tgttgctgta                                              20

<210> SEQ ID NO 3
<211> LENGTH: 20
<212> TYPE: DNA
<213> ORGANISM: Artificial Sequence
<220> FEATURE:
<223> OTHER INFORMATION: C4ST forward

<400> SEQUENCE: 3
gtggggagag ggagagaatc                                              20

<210> SEQ ID NO 4
<211> LENGTH: 20
<212> TYPE: DNA
<213> ORGANISM: Artificial Sequence
<220> FEATURE:
<223> OTHER INFORMATION: C4ST backward

<400> SEQUENCE: 4
acagacaaga acgacccatc                                              20

<210> SEQ ID NO 5
<211> LENGTH: 20
<212> TYPE: DNA
<213> ORGANISM: Artificial Sequence
<220> FEATURE:
<223> OTHER INFORMATION: C6S forward

<400> SEQUENCE: 5
cccaaagtca gaaagcgaag                                              20

<210> SEQ ID NO 6
<211> LENGTH: 20
<212> TYPE: DNA
```

```
<213> ORGANISM: Artificial Sequence
<220> FEATURE:
<223> OTHER INFORMATION: C6S backward

<400> SEQUENCE: 6
acaagcaaac ccaccaactc                                               20

<210> SEQ ID NO 7
<211> LENGTH: 20
<212> TYPE: DNA
<213> ORGANISM: Artificial Sequence
<220> FEATURE:
<223> OTHER INFORMATION: CS-2OST forward

<400> SEQUENCE: 7
tctgagcctg accacagatg                                               20

<210> SEQ ID NO 8
<211> LENGTH: 20
<212> TYPE: DNA
<213> ORGANISM: Artificial Sequence
<220> FEATURE:
<223> OTHER INFORMATION: CS-2OST backward

<400> SEQUENCE: 8
cacctgcaca gaactcagga                                               20

<210> SEQ ID NO 9
<211> LENGTH: 20
<212> TYPE: DNA
<213> ORGANISM: Artificial Sequence
<220> FEATURE:
<223> OTHER INFORMATION: NDST-1 forward

<400> SEQUENCE: 9
cccagtggcc ctaaagtaca                                               20

<210> SEQ ID NO 10
<211> LENGTH: 20
<212> TYPE: DNA
<213> ORGANISM: Artificial Sequence
<220> FEATURE:
<223> OTHER INFORMATION: NDST-1 backward

<400> SEQUENCE: 10
gtccatcact ttggcaggtt                                               20

<210> SEQ ID NO 11
<211> LENGTH: 20
<212> TYPE: DNA
<213> ORGANISM: Artificial Sequence
<220> FEATURE:
<223> OTHER INFORMATION: HS6S forward

<400> SEQUENCE: 11
gtacaacctg gccaacaacc                                               20

<210> SEQ ID NO 12
<211> LENGTH: 20
<212> TYPE: DNA
<213> ORGANISM: Artificial Sequence
<220> FEATURE:
<223> OTHER INFORMATION: HS6S backward

<400> SEQUENCE: 12
cgcgtgctat tgtactgcat                                               20
```